(12) United States Patent
Tavakkoli et al.

(10) Patent No.: US 12,166,948 B2
(45) Date of Patent: Dec. 10, 2024

(54) METHODS AND SYSTEMS FOR DIAGNOSING VISION LOSS AND PROVIDING VISUAL COMPENSATION

(71) Applicant: NEVADA RESEARCH & INNOVATION CORPORATION, Reno, NV (US)

(72) Inventors: Alireza Tavakkoli, Reno, NV (US); Stewart Zuckerbrod, Bellaire, TX (US)

(73) Assignee: NEVADA RESEARCH & INNOVATION CORPORATION, Reno, NV (US)

( * ) Notice: Subject to any disclaimer, the term of this patent is extended or adjusted under 35 U.S.C. 154(b) by 268 days.

(21) Appl. No.: 17/786,911

(22) PCT Filed: Dec. 23, 2020

(86) PCT No.: PCT/US2020/066843
§ 371 (c)(1),
(2) Date: Jun. 17, 2022

(87) PCT Pub. No.: WO2021/138198
PCT Pub. Date: Jul. 8, 2021

(65) Prior Publication Data
US 2023/0336703 A1    Oct. 19, 2023

Related U.S. Application Data

(60) Provisional application No. 62/955,554, filed on Dec. 31, 2019.

(51) Int. Cl.
*H04N 13/15*     (2018.01)
*A61B 3/10*      (2006.01)
(Continued)

(52) U.S. Cl.
CPC ............. *H04N 13/15* (2018.05); *G16H 50/30* (2018.01); *H04N 13/156* (2018.05);
(Continued)

(58) Field of Classification Search
USPC ......................................................... 382/128
See application file for complete search history.

(56) References Cited

U.S. PATENT DOCUMENTS

2017/0273552 A1* 9/2017 Leung .................... A61B 3/005
2018/0004002 A1* 1/2018 Rong ................. G02B 27/0176
(Continued)

OTHER PUBLICATIONS

Canadian Examiners Report dated Aug. 9, 2023 which was issue in connection with Canadian Patent Application No. 3,163,545. 5 pages.
(Continued)

*Primary Examiner* — Darryl V Dottin
(74) *Attorney, Agent, or Firm* — Buckley, Maschoff & Talwalkar LLC

(57) ABSTRACT

Methods, systems and apparatus for compensating vision loss for a patient. In some embodiments, a computer processor receives vision loss data associated with a vision loss region of an eye of a patient from a head mounted display (HMD) device worn by the patient, generates a parameterized perceptual loss model, and then generates inverse data to correct for color loss, contrast and luminance desaturation, and visual rotational and spatial distortion suffered by the eye of the patient. The computer processor then transmits the inverse data to the HMD device being worn by the patient for use in correcting the visual rotational and spatial distortion loss of the eye of the patient.

18 Claims, 11 Drawing Sheets

(51) Int. Cl.
    *G16H 50/30*         (2018.01)
    *H04N 13/00*         (2018.01)
    *H04N 13/156*       (2018.01)
    *H04N 13/344*       (2018.01)

(52) U.S. Cl.
    CPC ............ *H04N 13/344* (2018.05); *A61B 3/102* (2013.01); *H04N 2013/0077* (2013.01)

(56) References Cited

U.S. PATENT DOCUMENTS

| | | |
|---|---|---|
| 2018/0160896 A1 | 6/2018 | Nordstrom |
| 2018/0249151 A1 | 8/2018 | Freeman et al. |

OTHER PUBLICATIONS

"Tthe International Search Report and Written Opinion" dated Mar. 15, 2021 which is issued in connection with PCT Application No. PCT/US20/66843.

Canadian Examiners Report dated Jun. 14, 2024 which was issue in connection with Canadian Patent Application No. 3,163,545. 5 pages.

\* cited by examiner

METHODS AND SYSTEMS FOR DIAGNOSING VISION LOSS AND PROVIDING VISUAL COMPENSATION

CROSS REFERENCE TO RELATED APPLICATIONS

This application is a U.S. National Stage patent application and claims the benefit of International Patent Application No. PCT/US2020/066843 filed on Dec. 23, 2020, which claims the benefit of U.S. Provisional Patent Application No. 62/955,554 filed on Dec. 31, 2019, the contents of which are hereby incorporated by reference for all purposes.

FIELD OF THE INVENTION

Methods and apparatus for systematically examining and obtaining vision loss data associated with a specific neuro-ocular condition, wherein the vision loss data includes physiological vision data such as optical coherence tomography (OCT) data, fundoscopy data, and functional vision data such as acuity level data, color and contrast sensitivity data, visual distortion data, and visual field loss data of a patient. In implementations, the vision loss data is used to deliver specialized visual aid to that patient. Specifically, the patient is fitted with a head mounted display (HMD) device that provides the visual aid to correct the specific area(s) of vision deficit.

BACKGROUND

There are several components of vision that contribute to a person's overall level of visual function including visual quantity and visual quality measures. Visual quantity is determined by a person's visual acuity and visual field results, whereas visual quality is the person's function in vision-related activities and provides the clinician a better understanding of how the patient is able to use their vision for daily living activities. Physicians typically administer a contrast sensitivity test to evaluate a patient's quality of vision. Contrast sensitivity evaluates vision over a range of spatial frequencies and contrast levels. In addition to helping predict a patient's contrast and magnification needs, contrast sensitivity also helps predict the success with optical devices. Although visual acuity and field testing to quantify optical errors has been successful, they fail to provide any measurements on neural errors.

There are various age-related eye diseases and conditions that can drastically affect a person's quality of life by causing permanent vision loss. Such diseases include Age-related Macular Degeneration (AMD), Diabetic Eye Diseases, and Glaucoma. According to the National Eye Institute an estimated thirty-seven million adults in the United States over the age of forty suffer from an age-related eye condition, such as AMD, Glaucoma, Diabetic Retinopathy, and Cataracts. Surgical procedures are available for effectively removing cataracts and treating patients, but for other age-related conditions, such as AMD and some other retinal diseases, there are no effective treatments to completely recover lost vision.

Diabetic Retinopathy is the most common cause of vision loss in people with diabetes whereas advanced AMD, which causes progressive visual impairment, is the leading cause of irreversible blindness and visual impairment in otherwise healthy individuals in the United States. The blindness caused by Diabetic Retinopathy and by AMD is due to damage to the patient's retina resulting in central vision loss. In contrast, the damage caused to the optic nerve by Glaucoma produces gradual loss of peripheral vision in one or both eyes of a patient. There is no current treatment for AMD, and the only means of improving the lives of individuals suffering from that disease is via assistive technologies.

A barrier impeding progress in this area is the lack of understanding of the nature, and the extent, of correlations between ocular physiology and visual function. Ocular diseases cause physiological and structural changes to the visual system, which in turn present functional impacts on the patient's vision. Tests are currently available that provide physicians with the physiological impacts of the affected area within the eye of patients with AMD and other neural diseases of the eye, but such tests fall short of providing a measurement of the perceptual impact on a particular patient's vision. In addition, although the location and the physiological extent of the damage to the retina can be determined, the currently available assistive technologies do not utilize this information to provide sight specific visual aid because a number of barriers exist which prevent the current assistive technologies from providing each patient with individualized and/or specialized assistance for enhancing his or her remaining vision.

For example, commercially available kits attempt to simulate various vision loss phenomena using goggles with easily changeable lenses to simulate different anomalies. Although such techniques (such as the ones that use goggles) are inexpensive, setting up of the device is rather cumbersome and each disease requires a different hardware setup. Moreover, once set and built the goggles cannot be modified and thus lose their effectiveness for the patient as the disease progresses. Thus, software-based simulation techniques have been developed to provide interactive ways to simulate various impairments online. However, these simulations work on a regular monitor and typically fall short of providing a complete binocular and stereoscopic simulation, and thus do not provide an accurate and immersive representation of the patient's visual loss.

Augmented Reality (AR) environments could be employed to deliver a more accurate simulation of the visual impairment of patients, and a simulator of several visual impairments for normally sighted individuals has been developed. However, the existing AR systems cannot accurately model the perceptual loss caused by actual physiological damage impacting an individual's retina. Thus, conventional AR systems are unsuitable for accurately modeling a patient's perceptual vision loss and thus are not capable of being used by a patient to recover functional vision loss caused by a disease such as AMD.

The inventors recognized that there is a need for methods and systems that can provide an understanding of the relationship between ocular function and its physiology, and a need for effective interventions to compensate for the lost function. Specifically, there is a need for a vision loss process which includes systematically examining and determining how the acuity level, visual distortions, and visual field loss of a patient is associated with a specific eye condition, and for an apparatus and/or system that utilizes the resultant vision loss data to deliver specialized visual aid to that patient.

BRIEF DESCRIPTION OF THE DRAWINGS

Features and advantages of some embodiments of the present disclosure, and the manner in which the same are accomplished, will become more readily apparent upon consideration of the following detailed description taken in conjunction with the accompanying drawings, which illustrate preferred and example embodiments and which are not necessarily drawn to scale, wherein.

DETAILED DESCRIPTION

Reference will now be made in detail to various novel embodiments, examples of which are illustrated in the accompanying drawings. The drawings and descriptions thereof are not intended to limit the invention to any particular embodiment(s). On the contrary, the descriptions provided herein are intended to cover alternatives, modifications, and equivalents thereof. In the following description, numerous specific details are set forth in order to provide a thorough understanding of the various embodiments, but some or all of the embodiments may be practiced without some or all of the specific details. In other instances, well-known process operations have not been described in detail in order not to unnecessarily obscure novel aspects.

In general, and for the purposes of introducing concepts of embodiments of the present disclosure, disclosed herein are methods that provide a methodology which accurately generates a parametric model of the perceptual deficit caused by the physiological deterioration of a patient's retina, for example, due to Age-related Macular Degeneration (AMD). In addition, based on the parameters of the parametric model, a mechanism is described which simulates the patient's perception as a result of the eye disease. The simulation effectively delivers or provides the patient's eye doctor with an indication of the perceptual loss experienced by the patient and the progression of the eye disease for review.

In another aspect, disclosed is a mixed-reality (MR) apparatus and interface (which may take the form of a MR headset or head-mounted display (HMD) device that fits over the eyes of a patient) that compensates for the perceptual vision loss caused by the physiological damage to the patient, and thus permits the patient to recover functional vision. In some implementations, a visual test quantifies the distortions in the visual field via use of Virtual Reality Head-Mounted Displays (VR-HMD). In addition, VR-HMD mediated visual field perimetry and contrast sensitivity tests may be administered. Using these tests together beneficially delivers an improved comprehensive view of the patient's quality and quantity of visual function as compared to conventional methods. Although the main focus of the present disclosure is treating central vision loss caused by eye diseases such as AMD and Diabetic Retinopathy, it should be understood that the disclosed methodologies can be expanded to also cover and/or treat peripheral vision loss caused by eye diseases such as Glaucoma. Thus, the apparatus and methodologies disclosed herein apply to any neuro-ocular disorder affecting the retina, the optic nerve, or the visual cortex that cause neural errors and result in functional vision losses.

Figure 1A:
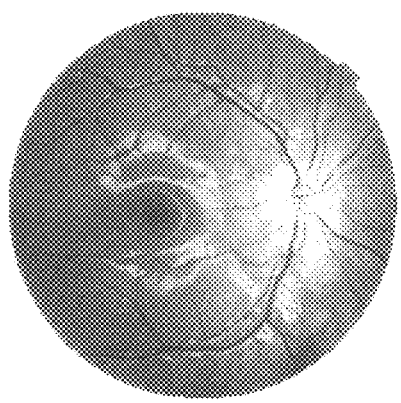
FIGS. 1A and 1B are images illustrating a healthy retina and a damaged retina, respectively, of a patient suffering from Age-related Macular Degeneration (AMD)
Figure 1B:
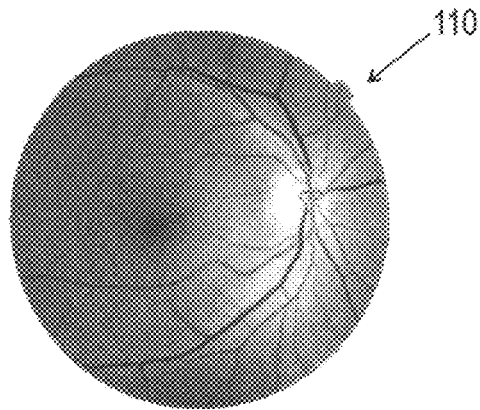
Figure 2A:
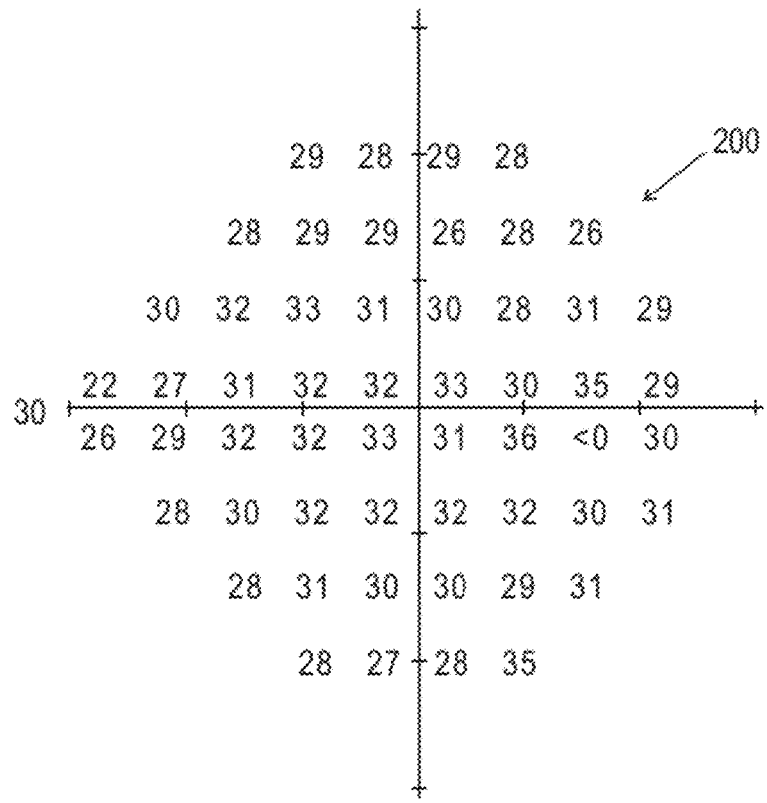
FIGS. 2A and 2B depict visual field perimetry results of a patient which can be used by Physicians to determine the physiological damage caused by the eye disease and to track the progression of the condition.
Figure 2B:
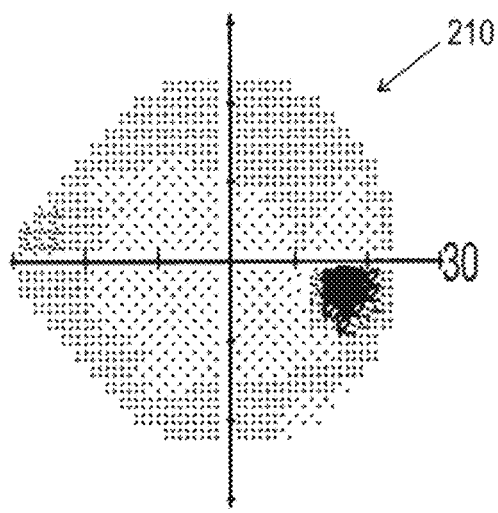
Figure 3A:
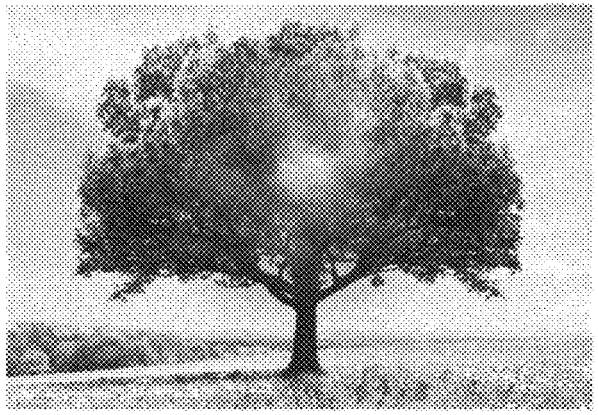
FIGS. 3A, 3B, 3C and 3D are images illustrating different types of perceptual effects in a patient's vision.
Figure 3B:
Figure 3C:
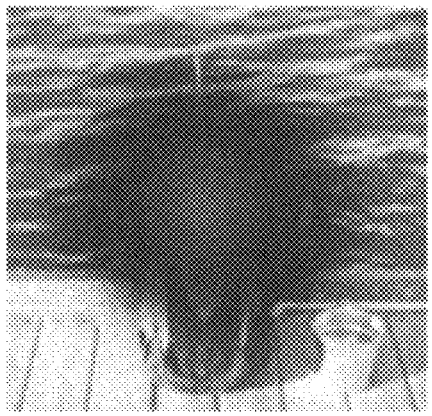
Figure 3D:

Fundus photography is a diagnostic tool that a physician can utilize to determine the physiological damage caused to the retina of a patient suffering from AMD. FIGS. 1A and 1B illustrate a healthy retina 100 and a damaged retina 110 of a patient suffering from AMD. FIGS. 2A and 2B depict visual field perimetry results 200 and 210, respectively, of a patient which can be used by Physicians to determine the physiological damage caused by the eye disease and to track the progression of the condition. However, it is difficult to interpret the perceptual impact of the physical damage. For example, AMD can cause a number of different types of perceptual effects in a patient's vision, such as those shown in FIGS. 3A, 3B, 3C and 3D. Therefore, a perceptual deficit model must provide data that accurately represents what the patient sees as a result of the physical damage to the retina.

Wearable Augmented Reality (AR) head-mounted display (HMD) technology is still in its infancy, and although potentially useful for treating eye disease symptoms, such devices can be expensive and thus potentially out of reach financially for many patients. Thus, presented herein are methods and apparatus which leverage on advances in the fields of Virtual Reality (VR) and Computer Vision (CV) in conjunction with the knowledge from current practices in the field of Ophthalmology to provide a unified infrastructure allowing for both simulation and vision recovery. In some embodiments, a patient generates a parameterized model for the perceptual deficit Some embodiments are based on a parametric model for the perceptual loss that includes a 4-tuple of the following form:

$$\mathcal{P} = (\Gamma, \Omega_\lambda, R_\theta, \Psi) \quad (1)$$

Where $\Gamma$ represents luminance degradation, $\Omega_\lambda$ represents a parametrization of the visual loss region in the field of vision of the patient with $\lambda$ as the cut-off value for the degradation determining the boundaries of $\Omega_\lambda$, $R_\theta$ is the rotational distortion matrix within $\Omega_\lambda$, and $\Psi$ is the Sinusoidal mapping function representing the spatial distortion.

With regard to modeling luminance degradation effects, a Gaussian Mixture Model (GMM) can be used as a representative model for the degradation in luminance caused as a result of damage to the cone photoreceptors. Therefore, the proposed model for luminance degradation, $\Gamma$, will be of the following form:

$$\Gamma = \Sigma_{i=1}^N \omega_i \cdot \mathcal{N}_{\overline{\mu_i},\sigma_i}(u,v) \quad (2)$$

Wherein u and v are the coordinate locations on the 2-D visual field, N is the number of Gaussian kernels (Normal distributions) modeling the deficit in the luminance perception in the visual field, and $\omega_i$ is the amount of luminance deficit caused by each Gaussian kernel. Each Gaussian is represented by $\mathcal{N}_{\overline{\mu_i},\sigma_i}(\bullet)$, where $\vec{\mu}_i = [\mu_i^u, \mu_i^v]$ represents the center and $\sigma$ represents the standard deviation of the distribution.

Figure 4A:
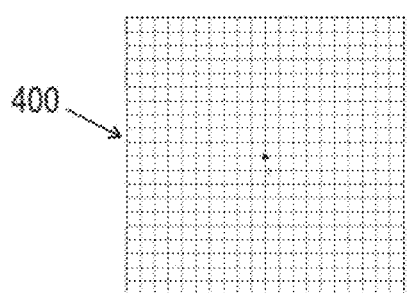
FIGS. 4A to 4D illustrate results of an embodiment of the illumination degradation model in affecting the vision on an Amsler grid in accordance with embodiments of the disclosure.
Figure 4B:
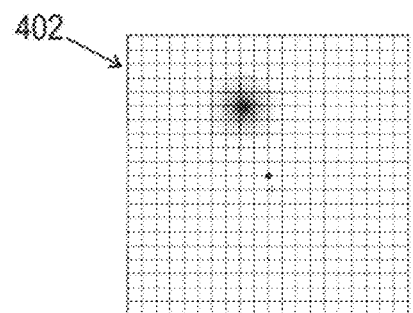
Figure 4C:
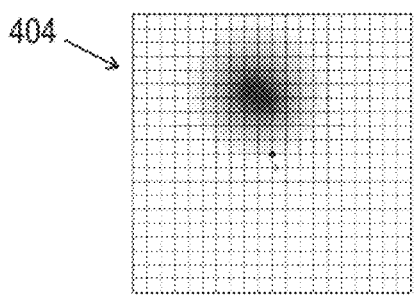
Figure 4D:
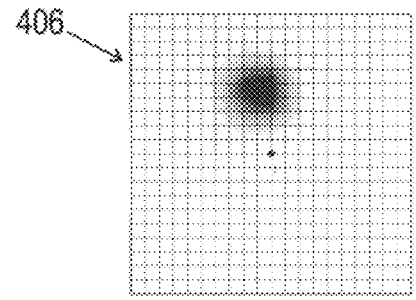

FIGS. 4A to 4D show the results of an embodiment of an illumination degradation model in affecting the vision on an Amsler grid in accordance with methods disclosed herein. As shown in FIG. 4A, an Amsler grid 400 is a tool that eye doctors typically use to detect vision problems resulting from damage to the macula (or central part of the retina) or the optic nerve. Specifically, FIG. 4B shows the illumination degradation 402 modeled by a single Gaussian. A significant advantage of the proposed parametric model is in its ability to represent complex illumination degradations caused by the progressive retina damage. As shown in FIGS. 4C and 4D, with the progression of the disease a more complex mathematical formulation is utilized instead of a single Gaussian to model the degradation. Specifically, FIG. 4C shows the illumination degradation 404 modeled by a double Gaussian formulation, whereas FIG. 4D shows the illumination degradation 406 modeled by a triple Gaussian formulation. Note that for each Gaussian kernel, the luminance deficit or luminance desaturation is the highest at the central location of that kernel.

Once the luminance degradation model is established (see Eq. (2) above), a region, designated "$\Omega$" as below, is determined in the visual field in which the perceptual impact is significant (See FIGS. 4A-4D). Accordingly, setting a cutoff value $0 < \lambda < 1$, the region $\Omega$ can be determined as follows:

$$\Omega = \{(u,v) \in \mathbb{R}_{[0,1]}^2 | \Gamma(u,v) \leq \lambda\} \quad (3)$$

Figure 5A:
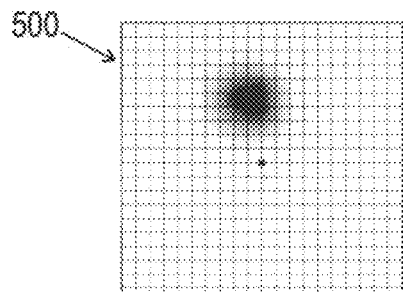
FIGS. 5A and 5B depict the perceptual deficit region Q represented by the disclosed parametric model in accordance with some embodiments of the disclosure.
Figure 5B:
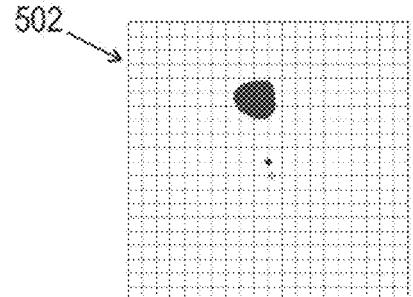
Figure 5C:
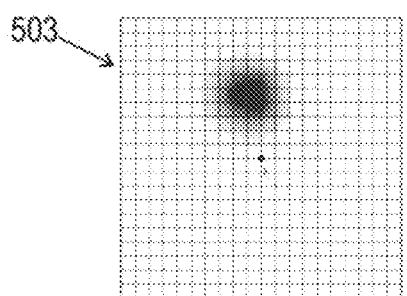
FIGS. 5C and 5D illustrate a perceptual deficit region Q different from that shown in FIGS. 5A and 5B, which includes various levels of degradation prominence k in accordance with some embodiments of the disclosure.
Figure 5D:
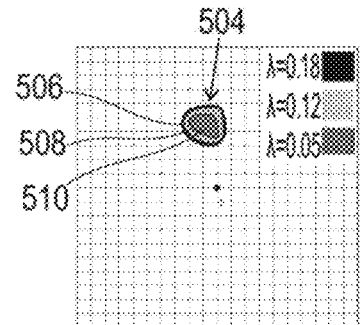

FIGS. 5A and 5B depict the perceptual deficit region $\Omega$ represented by the disclosed parametric model, wherein the area within the solid regions 500 and 502 represent illumination degradation of more than $\lambda$ percent. Specifically, the solid area 502 in FIG. 5B shows the perceptual deficit region $\Omega$, for the modelled illumination degradation illustrated in FIGS. 4A-4D, and since $\lambda$ is a free parameter, it can control the boundary of the perceptual deficit region $\Omega$. Thus, the larger the value of $\lambda$, the broader the region $\Omega$ will be. Broader regions with different prominent levels of illumination degradation, such as the region 504 shown in FIG. 5D, can also be visualized. Specifically, FIGS. 5C and 5D illustrate a different perceptual deficit region $\Omega$, labeled 503 and 504, which includes various levels of degradation prominence $\lambda$. In particular, the areas 506, 508 and 510 shown in FIG. 5D represent illumination degradation of more than $\lambda=18\%$, $\lambda=12\%$, and $\lambda=5\%$, respectively.

The Loci of the perceptual damage may be determined by the central positions ($\mu_i$) of each Gaussian distribution in Eq. (2), and the rotational distortion can be modeled as a result of physiological damage. As illustrated by Eq. (1), the rotational distortion, Re, is one of the components of the perceptual loss model, P. When $\theta$ is set as the angle of rotation, each point in the visual field will be rotated by the following rotation matrix:

$$\hat{R}_\theta = \begin{bmatrix} \cos\theta & -\sin\theta \\ \sin\theta & \cos\theta \end{bmatrix} \quad (4)$$

However, since the perceptual impact decreases as one moves farther away from the central location of each Gaussian kernel, the rotational distortion becomes less and less prominent. Therefore, the rotational distortion within the damaged region Q for each of the Gaussian kernels is modeled as:

$$R_\theta = \Sigma_{i=1}^N \omega_i \cdot \mathcal{N}_{\overline{\mu_i},\sigma_i}(u,v) \cdot \hat{R}_\theta \quad (5)$$

Figure 6A:
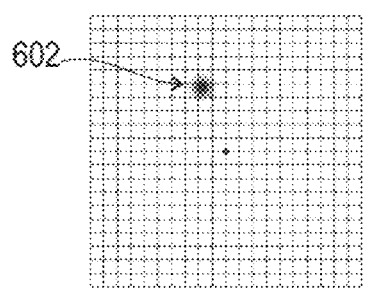
FIGS. 6A-6D are Amsler grids illustrating modeling of rotational distortion in accordance with some embodiments of the disclosure.
Figure 6B:
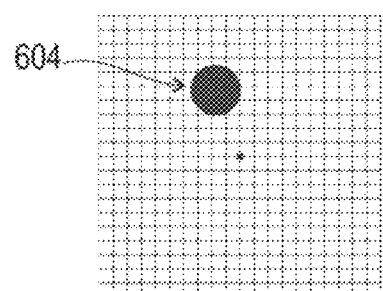
Figure 6C:
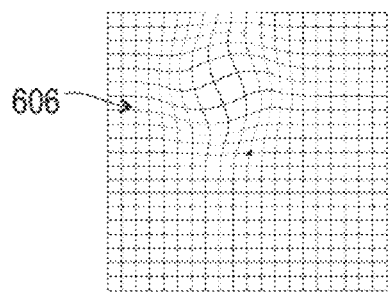
Figure 6D:
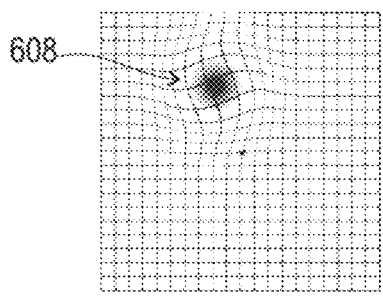

The effects of the rotational distortion within the affected region of the patient's visual field are shown in FIGS. 6A-6D, which illustrate modeling rotational distortion. Specifically, FIG. 6A shows a single Gaussian kernel illumination degradation 602 with FIG. 6B illustrating a perceptual impact region 604 with $\lambda=0.5$. FIG. 6C depicts a Rotational distortion 606 when the rotation angle $\theta=\pi/2$, wherein FIG. 6D illustrates both the illumination degradation and rotational distortion 608 as a result of the progression of the eye disease.

Figure 7A:
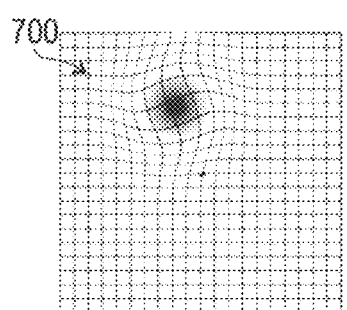
FIGS. 7A-7C are Amsler grids illustrating the rotational distortion and illumination degradation as the patient's eye disease progresses.
Figure 7B:
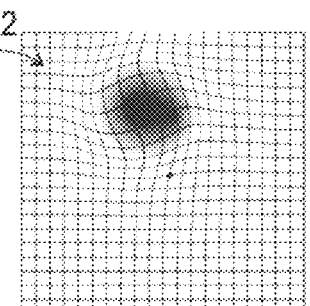
Figure 7C:
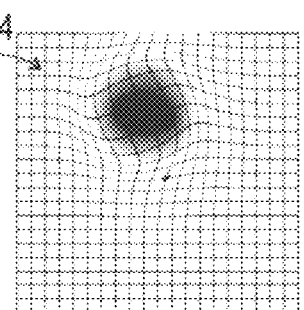

FIGS. 7A-7C illustrate the rotational distortion and illumination degradation 700, 702 and 704 as the disease progresses. Thus, the proposed parameterized framework can advantageously model the progression of both the illumination degradation and rotational distortion as a result of the disease progression.

The final component of the perceptual deficit is the spatial distortion model $\Psi$. This model represents the spatial shift perceived by the patient as a result of the damage to the retina that is not captured by the rotational distortion model described above. The spatial distortion model may be represented by a vector field dictating the spatial translation of points within the visual field, and the complete spatial distortion vector field $\Psi$ may be defined as:

$$\Psi = \sum_{i=1}^{N} \mathcal{N}_{\mu_i}^{i}(u, v) \cdot I_2 \cdot \begin{bmatrix} (u - \mu_i^u) \\ (v - \mu_i^v) \end{bmatrix} \quad (6)$$

wherein $N_i$ represents each of the Gaussian deficit models with the mean of $\mu_i$ and the standard deviation of $\sigma_i$. $I_2$ represents the 2×2 identity matrix, and u and v are coordinates within the visual field. To illustrate this spatial distortion effect, if a single scotoma is present at the central location of the visual field (i.e., $[u \; v]^T = 0$). The vector field representing the spatial distortion model will be of the following form (and shown in FIGS. 8A and 8B):

$$\Psi \approx \begin{bmatrix} e^{-\frac{(u-\mu_u)^2}{2\sigma^2}} (u - \mu_i^u) \\ e^{-\frac{(v-\mu_v)^2}{2\sigma^2}} (v - \mu_i^v) \end{bmatrix} \quad (7)$$

Figure 8A:
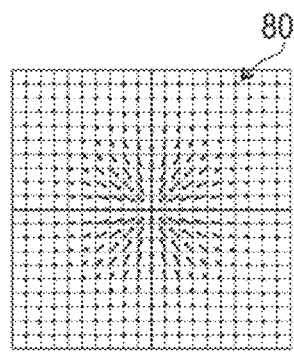
FIGS. 8A and 8B illustrate the vector fields representing the spatial transformations that the patient's visual field undergoes as a result of the physiological damage.
Figure 8B:
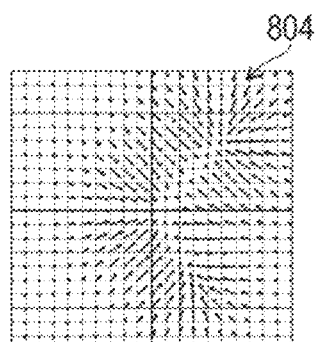

FIGS. 8A and 8B illustrate the vector fields 802 and 804 that represent the spatial transformations that the visual field undergoes as a result of the physiological damage. A single Gaussian kernel will generate a simple vector field 802, while a more complex spatial distortion 804 requires a Gaussian Mixture Model.

Figure 9A:
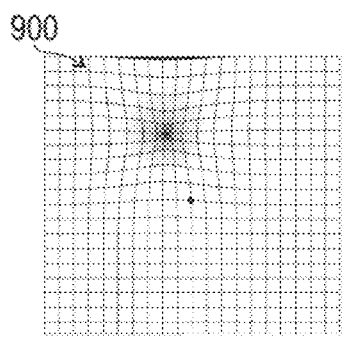
FIGS. 9A-9C illustrate the strength of an embodiment of the model for representing the spatial distortions caused by the eye disease on the Amsler grid in accordance with some embodiments of the disclosure.
Figure 9B:
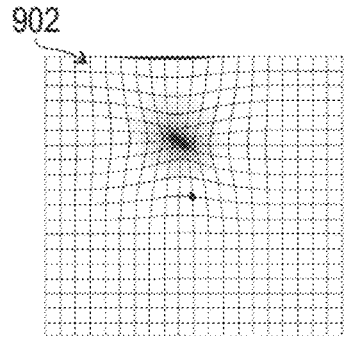
Figure 9C:
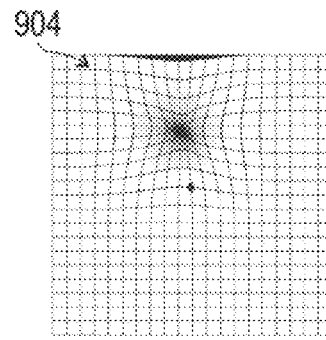

FIGS. 9A-9C illustrate the strength of the proposed model for representing the spatial distortions caused by the eye disease on the Amsler grid as represented by the $\Psi$ component of the proposed model. FIG. 9A illustrates the distortions 902 present during the early stages of the eye disease, which can be modeled using a single Gaussian kernel. However, as the eye disease progresses more complex models will be required. Thus, the proposed mixture model, which allows flexibility when representing the distortions, changes as the eye disease progresses without needing to fundamentally change the model. Instead, the number of Gaussian kernels increase to provide the distortion representations 904 and 906 on the Amsler grid as shown in FIGS. 9B and 9C, respectively. Accordingly, the model adaptation disclosed herein advantageously captures the eye disease progression of a patient by modeling spatial distortion first with a single Gaussian kernel as shown in FIG. 9A, then with two Gaussian kernels as shown in FIG. 9B, and with three Gaussian kernels as shown in FIG. 9C.

Figure 10A:
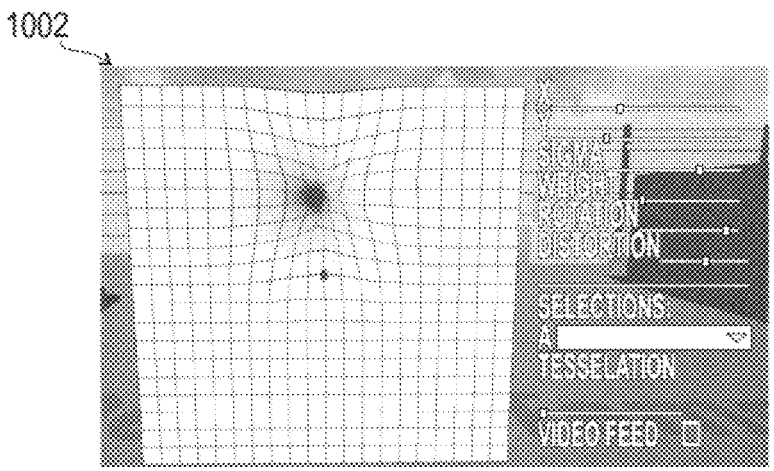
FIG. 10A is a diagnostic interface which allows a patient to establish the perceptual deficit model for his or her eyes on an Amsler grid and then populate the parameters in a Diagnostic VR environment in accordance with some embodiments of the disclosure.
Figure 10B:
FIG. 10B is an example of a functional vision recovery video feed that is generated based on the perceptual deficit model data established by the patient in accordance with some embodiments of the disclosure.

FIG. 10A shows the diagnostic interface 1002 which allows a patient to establish the perceptual deficit model for his or her eyes on an Amsler grid and then populate the parameters in a Diagnostic VR environment. FIG. 10B illustrates a functional vision recovery video feed 1004 from a webcam that is generated based on the perceptual deficit model data established by the patient, which is then mapped to the patient's eyes to correct the patient's perceptual deficit.

Figure 11:
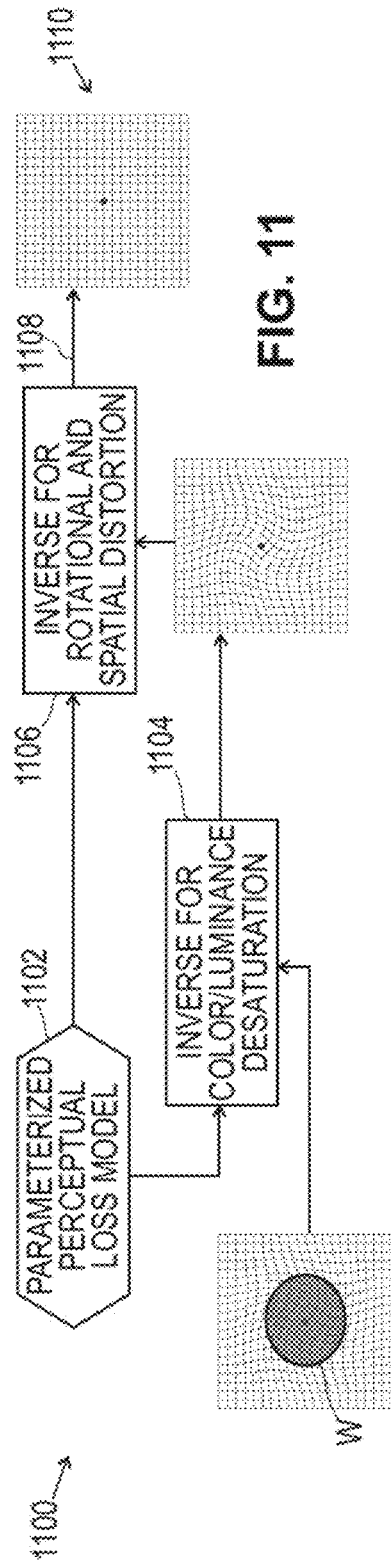
FIG. 11 is a block diagram illustrating an embodiment of a dichoptic solution and/or process for vision compensation in accordance with some embodiments of the disclosure.

FIG. 11 is a block diagram 1100 illustrating a dichoptic solution (for both eyes of a patient) and/or process for vision compensation which involves enhancing and/or correcting the remaining vision in the affected eye of a patient suffering from an eye disease. A vision loss region (W) is determined by providing the patient with an Amsler grid (as described above) in a neutral Virtual Reality (VR) environment, and then using VR googles or a head mounted display (HMD) device to test the vision of a patient and generate vision loss data for the affected eye based on the information provided by the patient. A computer or other electronic device including a processor or processors runs the parameterized perception loss model 1102, which utilizes the vision loss data of the patient received from the HMD device to generate 1104 inverse data for color and/or luminance desaturation, and to generate 1106 inverse data for rotational and spatial distortion for the affected eye of the patient. In some implementations, the computer processor transmits 1108 the inverse data for the color and/or luminance desaturation and the inverse data for the rotational and spatial distortion to the HMD device being worn by the patient, and then the HMD device utilizes this inverse data with regard to the affected eye of the patient to enhance and/or correct 1110 the perceptual loss of vision of the patient. In some embodiments, this process may be used for one or both eyes of the patient.

It should be understood that the model presented above covers only functional vision parameters and excludes color sensitivity, which is useful for basic perimetry focusing only on luminance (rod photoreceptor) responses. Thus, in some further embodiments explained below, a comprehensive model covers both functional vision and neuro-ocular physiology. In addition, in some implementations the model includes color sensitivity (cone photoreceptor responses) which provides a more comprehensive spatial rotation and distortion modeling. In some circumstances, the following model may be preferred to map a complete model of visual function and physiology of a patient, whereas the model presented above may be useful as an approximation mode. However, all of the models disclosed herein are effective for use as a neural compensation mechanism.

In some embodiments, a parameterized model for the affected vision of a patient in conjunction with visual function tests administered via VR is provided. However, the disclosed model for the functional vision loss ($\Lambda$) of a patient is a 5-tuple, and the physiological impact model ($\Phi$) is a triplet of the following forms:

$$\Lambda = (\Omega_\lambda, \Psi, \Theta, \Gamma, \Delta) \Phi = (\Omega_\phi, \Pi, \rho) \quad (8)$$

where $\Omega_\lambda$ and $\Omega_\phi$ represent a parametrization of the visual field loss region or visual loss region, and the physiological damage region, respectively; $\Psi$ represents the model of contrast sensitivity within $\Omega_\lambda$; $\Theta$ is the color sensitivity model within $\Omega_\lambda$; $\Gamma$ represents the distortion matrix, and $\Delta$ is the a mapping function representing the spatial distortion within the region $\Omega_\lambda$. $\Pi$ and $\rho$ are parameters of the physiological test determined based on the test and do not have a predefined format. For example, an OCT image of the optic nerve will be parameterized spatially by $\Pi$, while $\rho$ represents the number of shades in the image within the damaged region.

The first concern in modeling the damaged regions is identifying its boundary. This localization is achieved by utilizing the results from the patient to populate a multivariate model as a Gaussian Mixture Model (GMM):

$$\Omega_{\phi,\lambda}(N, \mu_i, \mu_i, \sigma_i): \mathbb{R}^2 \to \mathbb{R} \text{ for } i \in \{1, \ldots, N\} \quad (9)$$

With a boundary of $\partial_\Omega$ as follows:

$$\Omega_{\phi,\lambda} = \sum_{i=1}^{N} \exp\left(-\frac{(x-\mu_x^i)^2(y-\mu_y^i)^2}{2\sigma_x^{2i}\sigma_x^{2i}}\right) \text{ and } \partial\Omega : \Omega_{\phi,\lambda} = c \quad (10)$$

Wherein c is less than or equal to 1 is the boundary threshold. The following error is used for optimizing the GMM parameters:

$$Err = \frac{|W \cap V|}{|W| + |V|} \quad (11)$$

Wherein |•| is the area contained within a region. Thus, there is an optimization problem and therefore an evolutionary computing approach is used to solve for this optimization problem. The optimization solution will result in the parameters of the GMM minimizing the error in eq. (11).

Next, color and contrast sensitivity are modeled, and these parameters represent the contrast, as well as Red/Green/Blue color sensitivity of the patient in and around the area of the vision loss ($\Omega_\lambda$). Let ($\mu_x, \mu_y$) be the center and $\gamma_x^2$, $\gamma_y^2$ be the spread of the visual loss region in the x and y directions within the region Q, respectively. The contrast ($\Psi$) and color sensitivity ($\Theta$) can then be modeled as follows:

$$\begin{bmatrix}\Psi \\ \Theta\end{bmatrix}^T = \left[\alpha \cdot \tanh\left(\frac{(x-\mu_x)^2 + (y-\mu_y)^2}{\gamma_x^2 \gamma_y^2}\right)\right.$$
$$\left.\beta \cdot 1_{1\times 3} \cdot \tanh\left(\frac{(x-\mu_x)^2 + (y-\mu_y)^2}{\gamma_x^2 \gamma_y^2}\right)\right] \quad (12)$$

These equations formulate how the colors grow less vibrant and the contrast sensitivity of the perceived light decreases as we get closer to the center of the impacted region of the visual field of the patient. The patient will be able to control the parameters $\alpha$, $\beta$, $\gamma_x^2$ and $\gamma_y^2$ as a part the functional vision test delivered via the VR goggles or HMD device.

Next, rotation and spatial distortion are modeled. The distortion matrix ($\Gamma$) and spatial distortion mapping ($\Delta$) parameters are a matrix and a mapping responsible for the rotation and distortion of a rectangular gird (the Amsler grid), respectively. Let ($\mu_x, \mu_y$) be the center and $\sigma_x$ and $\sigma_y$ be the spread of the visual loss within the region $\Omega_\lambda$ in the x and y directions, respectively. The rotational parameter is then determined as:

$$\Delta_\theta = \begin{bmatrix}\cos\theta & -\sin\theta \\ \sin\theta & \cos\theta\end{bmatrix} \cdot \exp\left(-\frac{(x-\mu_x)^2(y-\mu_y)^2}{2\sigma_x^2 \sigma_y^2}\right) \quad (13)$$

Wherein $\theta$ is the parameter of the rotational distortion. The patient will be able to control this parameter via the distortion test, for each distortion within the distortion matrix of $\Gamma$. In order to formulate the spatial distortion matrix, two parameters are used: the center of spatial distortion, modelled as ($\rho_x, \rho_y$), and the spread of the spatial distortion, modeled as ($\delta_x, \delta_y$). The distortion parameter maps the Amsler grid onto a sinusoidal grid as follows:

$$\Gamma(\rho_x, \rho_y, \delta_x, \delta_y): \begin{bmatrix}x \\ y\end{bmatrix} \rightarrow \begin{bmatrix}\sin x \cdot \exp\left(-\frac{(x-\rho_x)^2}{2\delta_x^2 \delta_y^2}\right) \\ \sin y \cdot \exp\left(-\frac{(x-\rho_y)^2}{2\delta_x^2 \delta_y^2}\right)\end{bmatrix} \quad (14)$$

Thus, a parametric model of the patient's functional losses (and physiological ocular changes) is provided. The functional loss parameters are extracted from the functional tests while the parameters for the physiological impacts are determined from the physiological test results. These parametric models are utilized to develop a mapping between the pathophysiology of the ocular disease to its impact on the patient's functional vision.

Figure 12:
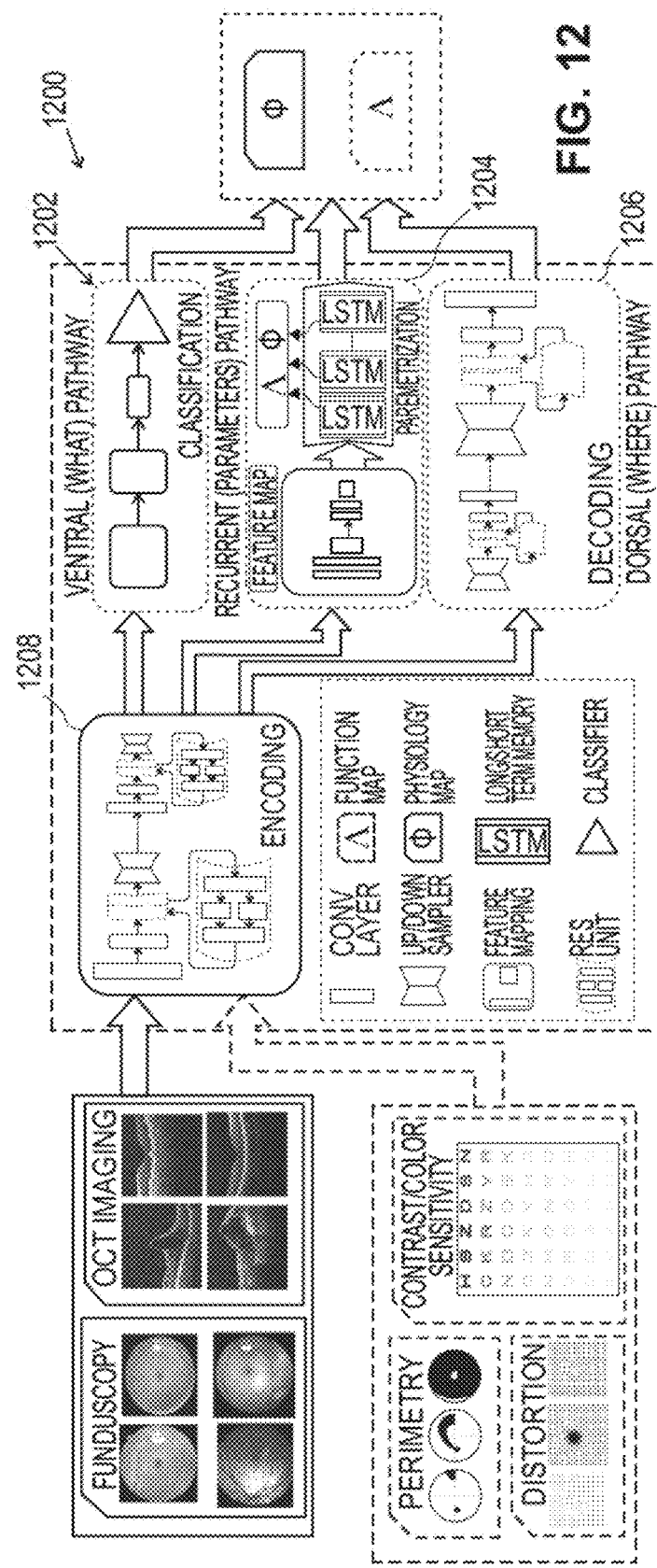
FIG. 12 is a block diagram of a framework for mapping the physiological parameters to the functional parameters of the impairment of the patient's eye in accordance with some embodiments of the disclosure.

FIG. 12 is a block diagram of a framework 1200 for mapping the physiological parameters to the functional parameters to develop a fundamental knowledge of the relationship between ocular structure and visual function of a patient. In some implementations, the framework 1200 includes a computational framework based in advances in the field of deep Convolutional Neural Networks (CNNs). Thus, in some embodiments a neural network with three distinct pathways may be utilized. As shown in FIG. 12, a first pathway 1202 is configured to classify the type of structural damage and functional loss, whereas a second pathway 1204 is configured to localize the damaged region of the patient's eye in the functional visual field, and the third pathway 1206 provides for parameterizing the physiological and functional losses. In some embodiments, the pathways 1202, 1204 and 1206 share an encoding component 1208, although different layers of the encoding mechanism may be utilized in the classification, localization, and parameterization components of the network.

In some embodiments, a convolutional neural encoder 1208 is provided which specializes in identifying retinal diseases with near perfect precision. Moreover, such an architecture may include a residual unit subsuming Atrous Separable Convolution, a building block and a mechanism to prevent gradient degradation. In particular, this novel approach in implementing the convolution will reduce the memory and computational complexity of the architecture while providing a mechanism to compensate for the degradation of the gradient as more layers are added to the network.

The Ventral Pathway or disease classification component 1202 of the network takes in the propagated batch through its convolutional layers, followed by batch-normalization to increase the network's regularization and rectified linear unit (ReLU) activations to improve the network ability to address non-linear decision boundaries, and fed-back into the network via a building block. Global average pooling can also be applied to the signals which passes through two more Fully Connected (FC) layers for the loss function. Such a network outperforms other conventional architectures with respect to the number of parameters, accuracy, and memory size and provides for the rapid identification of the eye disease with high or near perfect accuracy.

In some embodiments, a Dorsal Pathway of damage localization component 1206 may be configured to take decoded information and establish activation layer mappings for each anomaly within the input signal. Silencing techniques to suppress non-necessary filters activated by other normal structural components of the eye may be used to increase the damage localization performance.

In some implementations, the Recurrent Pathway or disease parametrization component 1204 of the network is configured to conduct high-level reentrant visual reasoning about the physiological and/or functional representation within the patient sensitivity profile, validated through the other two components (i.e., the dorsal pathway and ventral pathway components). In some embodiments, a number of input images are presented to the network, and contextual information (e.g., function/physiology parameters) from these images are encoded via the recurrence represented within this architecture.

The deep convolutional architecture is configured to produce a mapping between the results of functional tests (and functional parameters) and the results of the physiological tests (and parameters of the ocular change). Such a mapping allows for study of the correlations between ocular structure and functional vision to better understand the pathophysiology of neuro-ocular diseases.

Figure 13:
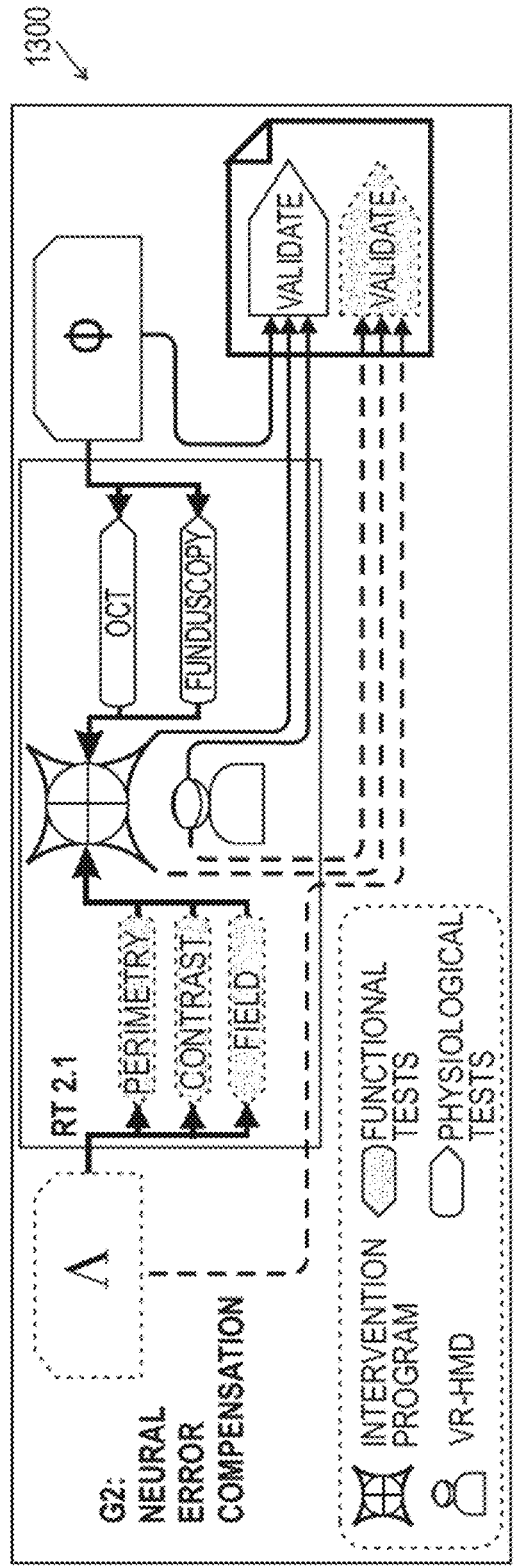
FIG. 13 is a block diagram of a structure for providing an effective mechanism that delivers a localized and binocular solution which helps the patient recover functional vision in accordance with some embodiments of the disclosure.

FIG. 13 is a block diagram of a structural flow 1300 for providing an effective mechanism that delivers a localized and binocular solution to the patient to help the patient recover functional vision. The parametric model is utilized to model the functional/physiological losses of the patient in order to allow for the recovery of functional vision. Loss parameters are utilized in the proposed intervention protocol to manipulate videos for each eye independently to invoke binocular interactions.

Figure 14:
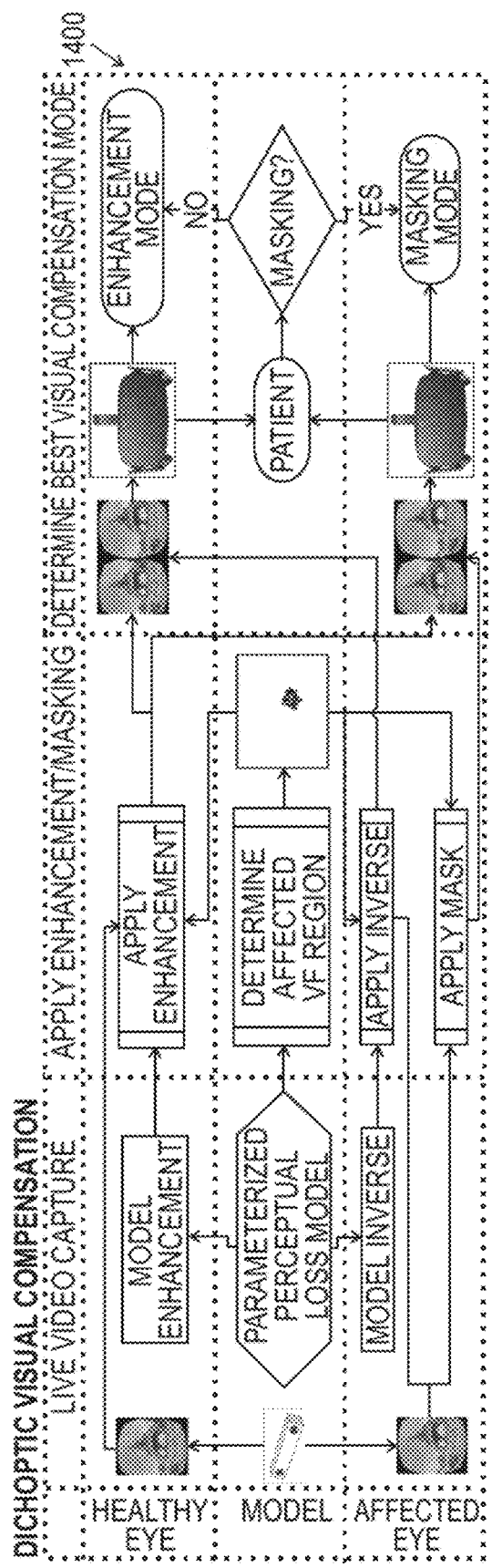
FIG. 14 is a flow diagram illustrating a dichoptic process for vision compensation in accordance with some embodiments of the disclosure.

FIG. 14 is a flow diagram illustrating a dichoptic process 1400 for vision compensation. In some embodiments, the dichoptic vision compensation process 1400 utilizes a first stereoscopic camera capturing left and right eye images for the patient. Next, the parametric perceptual loss model determines the vision loss region ($\Omega_\lambda$ and $\Omega_\phi$) and the parameters of the perceptual loss from the model $\Phi$ and the model $\Lambda$.

As mentioned above, an obstacle for addressing each patient's unique perceptual deficit is the ability to identify and target the affected area in which the deficit occurs. Thus, tasks associated with the identifying the perceptual losses and the mapping between these losses and the physiological changes to the eye are provided herein. With these models, a dichoptic mechanism can directly and effectively address the patient's vision loss. Typically, even in the case of bilateral diseases such as AMD, the affected regions of the patient's eyes are asymmetric, meaning that the visual loss occurs in different loci in each eye. As a result, the patient's vision can be enhanced by utilizing the unaffected regions from each eye independently.

Figure 15:
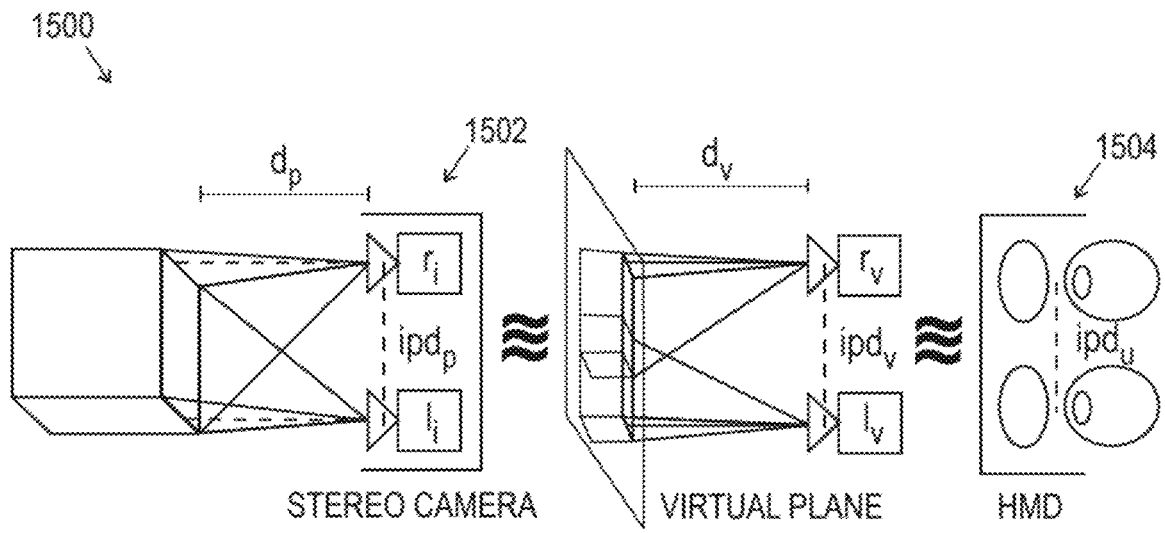
FIG. 15 is a functional block diagram illustrating the use of a stereoscopic camera system to capture videos from the real-world which are then manipulated and provided to a head mounted display (HMD) being used by a patient to correct and/or enhance the patient's vision in accordance with some embodiments of the disclosure.

FIG. 15 is a functional block diagram 1500 illustrating the use of a stereoscopic camera system 1502 to capture videos from the real-world which are then manipulated and provided to a head mounted display (HMD) 1504 being used by a patient to correct and/or enhance the patient's vision in accordance with processes described herein. Specifically, the videos captured by the stereoscopic camera system 1502 are manipulated by two independent processes based on the parameterized losses. The first process employs the parametric perceptual loss model to apply an inverse function to reverse the rotational and spatial distortions, and the color and luminance degradations in the affected region of the damaged eye. The second process utilizes the vision loss region (in the field of vision) of the non-affected eye to enhance (dichoptic enhancement) the quality of the image while masking the input of the vision loss region in the affected eye (dichoptic masking). The HMD 1504 being worn by the patient is fed data of both of these visual enhancement mechanisms for rendering to each eye of the patient in order to determine which option provides the most improvement.

Therefore, in some implementations in accordance with the methods disclosed herein, Virtual Reality (VR)-mediated equipment, such as VR headsets manufactured by Oculus, the HTC company, and/or Microsoft Corporation, may be utilized in addition to traditional equipment. It should be understood, however, that in some embodiments a customized VR headset and/or HMD device that includes a customized microprocessor chip and memory may be utilized with or without the addition of conventional equipment. Thus, functional visual assessments can be carried out via VR systems (which include a HMD device or VR goggles), standard clinical systems, and customized computer displays. Standard visual screenings can also be conducted by using a Metropsis™ system, which can provide clinical assessments for acuity, contrast sensitivity, color vision and stereovision. In some embodiments, a patient may be assessed for ocular dominance, contrast sensitivity, perceived contrast of supra-threshold stimuli, perceived blur, and binocular summation. In some implementations, the tests will be done monocularly through either eye and binocularly, to evaluate the effects of the enhancements on binocular interactions and for natural (binocular) viewing. Measurements can also be compared between the central (affected) and peripheral (healthy) loci to determine the efficacy of the image enhancement in cancelling the perceptual deficit. For example, contrast matching between Gabor patterns in the affected or unaffected area can be utilized to assess perceived contrast. Image quality may also be assessed by displaying natural images sampling a range of scenarios (e.g. faces, food, text, scenes) and asking patients to rate the quality with or without the enhancement, which results may be disseminated to the scientific and medical community for further assessment and evaluation.

Thus, in accordance with the methods described herein, patients suffering from Age-related Macular Degeneration (AMD), or other neural diseases of the eye, utilize embodiments of the discloses system(s) in two phases: a Virtual Reality (VR) Diagnostic phase, and an Augmented Reality (AR) Vision Compensation phase. In the first phase, the patient is fitted with VR goggles (or a head-mounted display (HMD) device) and shown an Amsler grid in a neutral VR environment to assess visual function. Thus, in some embodiments the patient interacts with a VR interface to pinpoint the parameters associated with the perceptual vision deficit. As the patient changes or updates his or her input parameters the scene being rendered for the patient's eyes changes in real-time. The goal is to have the patient closely mimic what he or she is seeing with their affected or diseased eye in order to populate the parameters of the perceptual deficit model of the affected eye. Once the patient accurately models the perceptual deficit, the remainder of the operation for recovering functional vision will take place in the augmented-reality (AR) vision compensation mode.

In AR vision compensation mode, the VR Head Mounted Display (HMD) works as AR glasses, by presenting the patient's eyes with live video of the environment captured through stereoscopic video cameras. The images in the stereoscopic video feed shown to the unaffected eye of the patient is, however, distorted by the perceptual loss model that the user provided in the VR diagnostic phase (the Amsler grid mode; see FIG. 10B). This gives the user an opportunity to test how the distortion looks in real life.

Thus, an uncorrected image of the vision of a patient can be observed by a physician so that the physician can then apply the inverse of the parametric model (as disclosed herein) so that the patient can see the environment as if the affected (diseased) eye were not impaired. Accordingly, based on the model generated by the proposed framework in the VR Diagnostics mode, an inverse function for the perceptual vision loss is calculated and then then applied in the AR mode to the live-stream videos recorded and rendered to each individual eye of the patient. This process is discussed with regard to FIG. 11, wherein the inverse function for the parametric vision loss compensates for the actual perceptual impact of the vision loss of the patient to recover as much functional vision for the patient as possible.

Figure 16A:
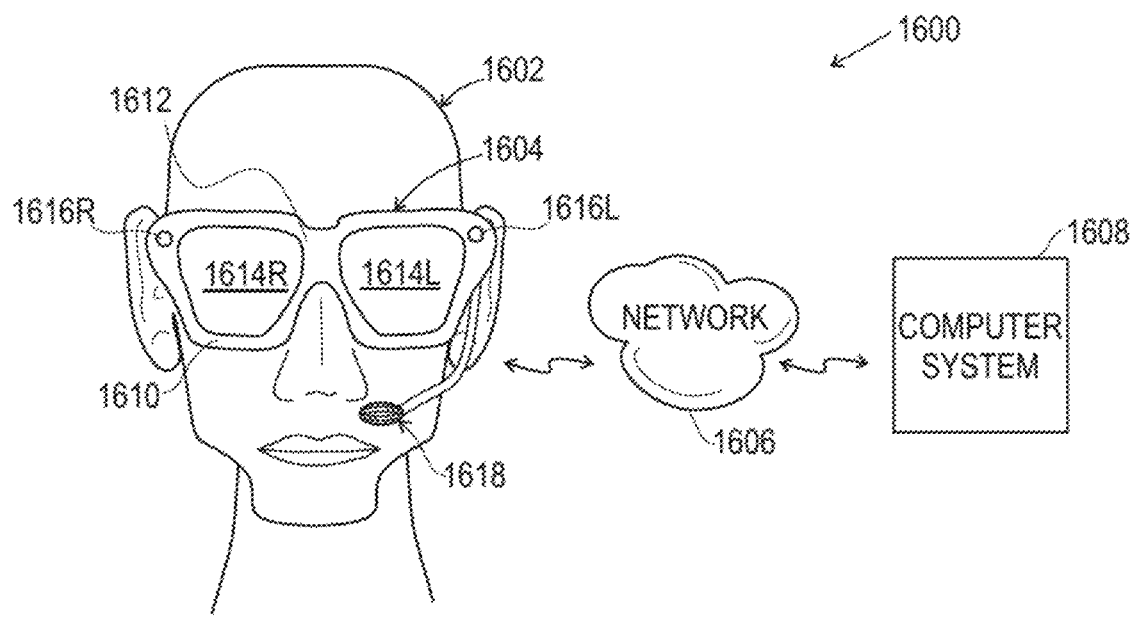
FIG. 16A is a block diagram of a visual aid system for delivering specialized visual aid to a patient in accordance with some embodiments of the disclosure.

FIG. 16A is a block diagram of a visual aid system 1600 for delivering specialized visual aid to a patient in accordance with some embodiments. The visual aid system includes a head mounted display (HMD) device 1604 fitted to the head of a patient 1602 and that is operably connected to a computer system 1608 via a network 1606, such as the Internet. The HMD device 1604 and/or the computer system 1608 can perform some or all of the methods and/or processes described herein. Although the HMD device 1604 is shown operably connected to the computer system 1608 via a network 1606, other embodiments are contemplated wherein these devices can wirelessly communicate with each other, while in some other configurations these components may be connected together via wires.

The visual aid system 1600 permits visual testing of a patient to quantify the distortions in the visual field of the patient via use of HMD device, and for administration of mediated visual field perimetry and contrast sensitivity tests. As mentioned herein, using these tests together beneficially delivers an improved comprehensive view of the patient's quality and quantity of visual function. Also, in addition to treating central vision loss caused by eye diseases such as AMD and Diabetic Retinopathy, peripheral vision loss caused by eye diseases such as Glaucoma can be treated.

Referring again to FIG. 16A, the HMD device 1604 includes a frame 1610 that includes a bridge 1612 configured for resting on the nose of a patient. The frame 1610 houses a first optical display 1614L positioned in front of the left eye of the patient, and a second optical display 1614R that is positioned in front of the right eye of the patient. The first optical display 1614L and second optical display 16146R are components of an image display system of the HMD device, and both include interior optical display surfaces (not shown). The interior optical display surfaces reflect light towards the patient's left eye and right eye, and include supporting electronic components (not shown).

The HMD device 1604 also includes a left camera 1616L and a right camera 1616R mounted to the frame, may include one or more sensors (not shown, such as light and/or temperature sensors), and a microphone 1618. The HMD device 1604 may also include an electronics module (not shown) or control circuitry for processing digital content (for example, images and/or video), and/or for gathering and/or processing data. The electronics module may include one or more processors and also be configured for optimizing the digital content to be presented to the patient, for analyzing data collected by the cameras and/or the one or more sensors, for analyzing patient audio responses received by the microphone 1618, and the like. In some embodiments, the electronics module and/or control circuitry may provide at least some data analysis functionality to be performed locally by the HMD device. The electronics module and HMD device can be powered by a battery (not shown), or through a wired or wireless connection to a power source (not shown).

The HMD device 1604 shown in FIG. 16A may be in the form of VR goggles, or a helmet, or a visor and the like. In accordance with methods described herein, the projection and presentation systems employed by the HMD device 1604 is binocular, meaning that the HMD device is configured for presenting a separate image to each of the wearer's eyes. In general, the HMD device is configured to display an image of a scene to the patient, obtain data from the patient concerning perceived vision loss, and in some embodiments transmit that vision loss data to a computer system 1608 for processing. In such embodiments, the HMD device 1604 next receives vision loss inverse data from the computer system 1608 which is utilized to correct for the perceived vision loss, and then the HMD device provides a live-stream video to correct the image of the scene to each eye of the patient. Specifically, the two cameras 1616L and 1616R mounted on the HMD device may be operable to take videos from the real world, one for each eye, and after performing an Inter-Pupilary Distance (IPD) correction, then apply appropriate masking on the object of interest in the video of the right and left images. In some embodiments, dichoptic masking is used, which involves using images from each of two stereoscopic cameras and their masks to form a constructed scene for a patient. Specifically, an image from the left camera 1616L and its mask and from the right camera 1616R and its mask of a scene are used to reconstruct the scene for the patient. Once the region of interest (ROI) is established, then the results of the parameterized perceptual modeling can be used to correct the region (or object) of interest in each eye independently. This allows for the binocular interaction to merge the left and right modified images to generate the scene effectively.

Referring to FIG. 16A, the HMD device 1604 may also include a microphone 1618 to receive audio input from a patient, which may be recorded and/or transmitted to the computer system 1608 for processing. In addition, in some embodiments the HMD device may include audio speakers such as over-ear headphones (not shown in FIG. 16A) that can be used to provide audio prompts, background music and/or atmospheric sounds and the like.

In some cases, the HMD device 1604 may be a specialized or customized VR headset or VR goggles for use by the patient that is specifically designed to obtain visual data and to correct the vision of the patient as described herein. Specifically, the electronics module of the HMD device may include a custom-made or specialized microprocessor or microprocessors operably connected to a storage device or memory storing processor-executable instructions which when executed cause the HMD device to function as disclosed herein. Accordingly, embodiments of an HMD device 1604 including such a specialized microprocessor are capable of obtaining data from the patient concerning perceived vision loss in one or both eyes, process that vision loss data locally and generate inverse data, and then utilize the inverse data to provide a live-stream video to each eye of the patient to correct the image of the scene for the patient. The electronics module may also include one or more processors for optimizing the digital content to be presented to the patient, for analyzing data collected by the cameras and/or the one or more sensors, for analyzing patient audio responses received by the microphone 1618, and the like.

In other instances, off-the-shelf HMD devices currently for sale by many manufacturers may be utilized to diagnose and correct vision loss of a patient. In particular, the various methods described herein could be performed using an HMD device that was designed for another purpose (for example, an HMD designed for gaming and/or other types of entertainment purposes). For example, in some implementations in accordance with the methods disclosed herein, VR headsets manufactured by Oculus, the HTC company, and/or Microsoft Corporation, may be utilized in addition to traditional equipment.

Referring again to FIG. 16A, the computer system 1608 may comprise a server computer, a client computer, a personal computer (PC), a tablet computer, a laptop computer, a personal digital assistant (PDA), a cellular telephone or Smartphone, a web appliance, a wearable electronic device, a gaming device, a music player, or any electronic device capable of executing a set of instructions (sequential or otherwise) that specify actions to be taken by the electronic device in accordance with methods disclosed herein. In some embodiments, the computer system includes one or more processors operably connected to a storage device, wherein the storage device includes processor-executable instructions which when executed cause the one or more processors to operate in accordance with processes described herein. In addition, in some implementations the visual aid processes for the patient can be distributed between the HMD device 1604 and the computer system 1608.

Figure 16B:
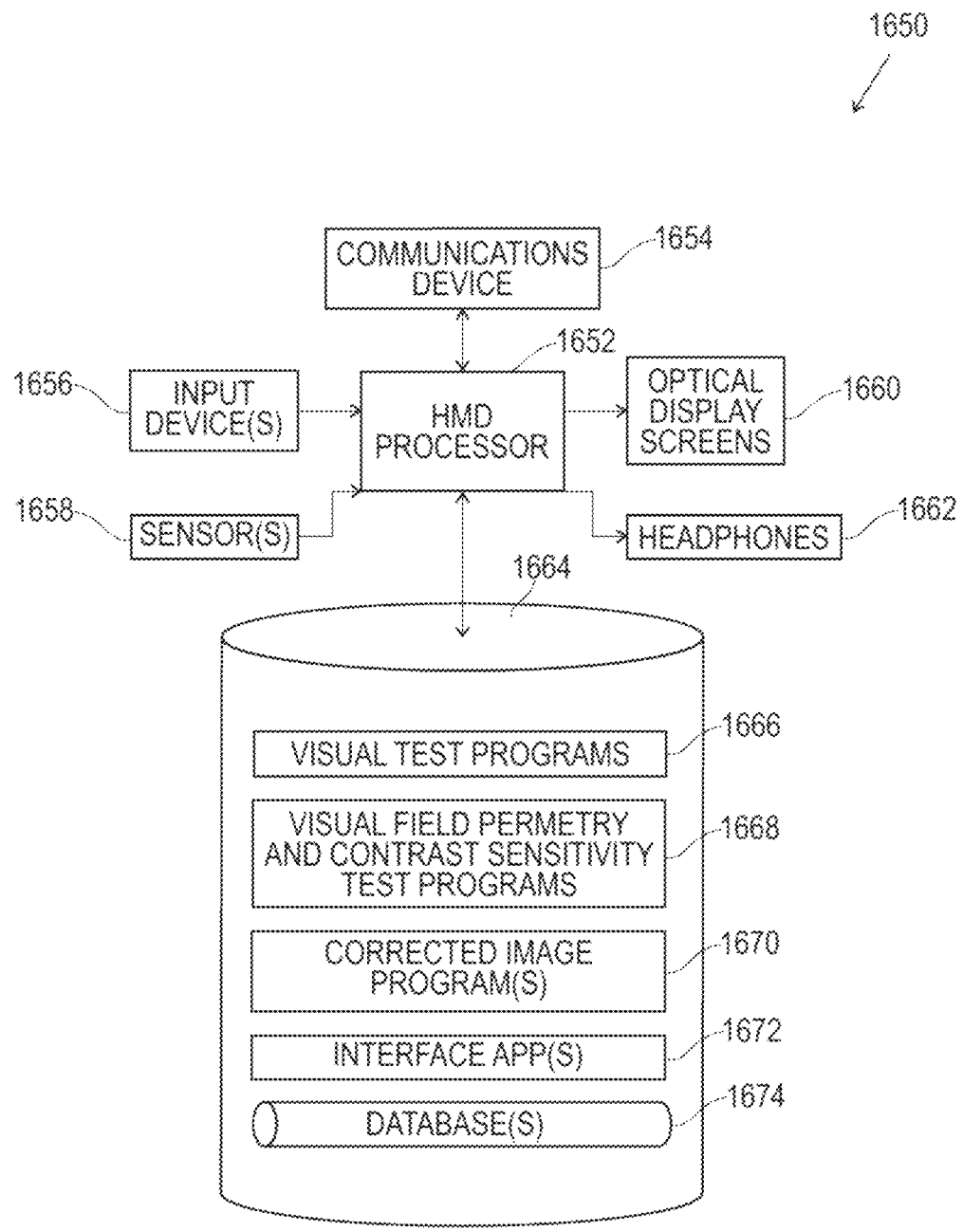
FIG. 16B is a block diagram of the components of an HMD device of a type that can operate in a manner consistent with some embodiments of the disclosure.

FIG. 16B is a block diagram 1650 of an example embodiment of the components of a HMD device of a type configured to operate in a manner consistent with processes described herein. The HMD device 1650 includes a HMD processor 1652 operatively coupled to a communication device 1654, one or more input devices 1656, one or more sensors 1658, optical display surfaces (one for each eye of a patient) 1660, headphones 1662 (or speakers; one for each ear of the patient), and a storage device 1664. The HMD processor 1652 may constitute one or more processors, which as mentioned earlier may be a custom designed microprocessor and/or a specialized microprocessor that is optimized to execute instructions and/or processor-executable steps, which may be contained in program instructions so as to control the HMD device 1650 to provide desired functionality.

The communication device 1654 may be used to facilitate communication with, for example, other electronic or digital devices such as other components of the system 1600 shown in FIG. 16A. Thus, communication device 1654 may comprise various and/or numerous communication ports (not separately shown), to allow the HMD device 1650 to communicate simultaneously with other computers or electronic devices, such as handheld electronic devices or server computers, and/or to simultaneously handle numerous functions. The communication device 1654 may also be configured for wireless communications and/or wired communications via various different types of networks, such as the Internet.

Referring again to FIG. 16B, the input devices 1656 may include one or more of any type of peripheral device typically used to input data into an HMD or to a computer. For example, the input device 1656 may include a microphone and/or hand controller(s) and/or a touchscreen. The input device 1656 may be utilized by the patient to provide one or more indications concerning his or her perceived vision loss while wearing the HMD device. The one or more sensors 1658 may include, for example, a camera and/or cameras, such as stereo cameras, to record a scene or the environment in front of the HMD device being worn by a patient, and/or a temperature sensor to record the temperature in the environment.

The storage device 1664 may be any appropriate information storage device, including combinations of magnetic storage devices (e.g., hard disk drives), optical storage devices such as CDs and/or DVDs, and/or semiconductor memory devices such as Random Access Memory (RAM) devices and Read Only Memory (ROM) devices, solid state drives (SSDs), as well as flash memory or other type of memory or storage device. Any one or more of such information storage devices may be considered to be a non-transitory computer-readable storage medium or computer usable medium or memory.

The storage device 1664 stores one or more processor executable instructions and/or computer programs and/or applications (Apps) for controlling the HMD processor 1652. The programs, program modules and/or Apps comprise program instructions (which may be referred to as computer readable program code means) that contain processor-executable process steps of the HMD device 1650 which are executed by the HMD processor 1652 to cause the HMD device 1650 to function as described herein.

The programs may include one or more conventional operating systems (not shown) that control the HMD processor 1652 so as to manage and coordinate activities and sharing of resources in the HMD device 1650, and to serve as a host for application programs that run on the HMD device 1650. The programs may also include visual test program(s) 1666 which may include, for example, processor-executable instructions for quantifying the distortions in the visual field of the patient. In addition, visual field perimetry and contrast sensitivity test programs 1668 and corrected image programs 1670 may be included. The corrected image programs function to provide a corrected image of a scene to the patient wearing the HMD device to compensate for the perceptual vision loss, and thus the various programs operate to allow the patient to recover functional vision. In addition, the storage device 1664 may also store interface applications 1672 which include executable instructions for providing software interfaces to facilitate interaction(s) between a patient and the HMD device and other components of a system, such as that shown in FIG. 16A. The storage device 1664 may also store one or more database(s) 1674 for storing patient data and/or other types of data. In addition, the storage device 1664 may store, and HMD device 1650 may execute, other programs which are not shown, for example, programs including HMD display device drivers, database management software, and the like. In addition, one or more further databases (not shown) which may be needed for operation of the HMD device 1650 may also be included.

Figure 17:
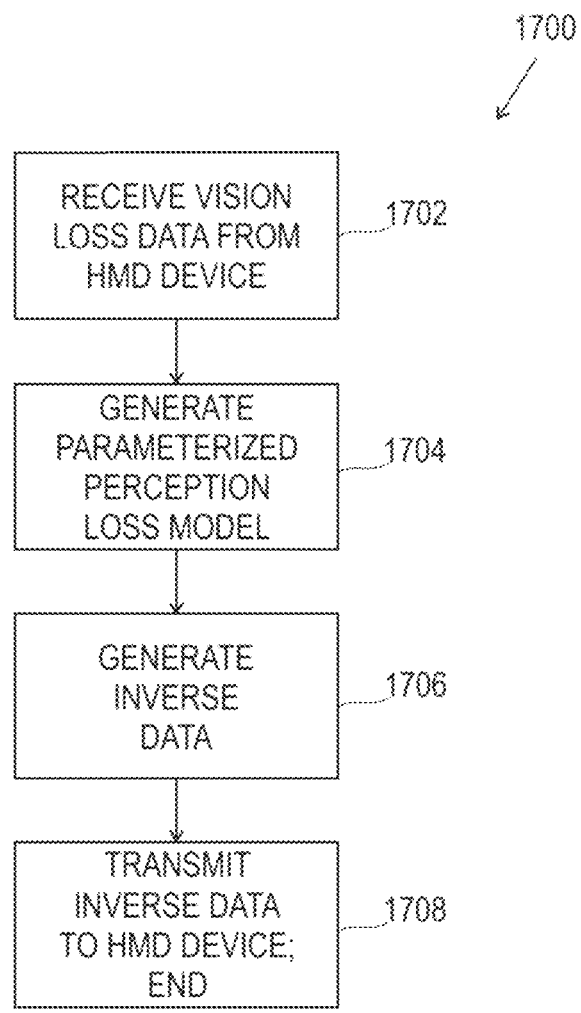
FIG. 17 is a flowchart of a process for compensating vision loss for a patient according to an embodiment of the disclosure.

FIG. 17 is a flowchart of a process 1700 for compensating vision loss for a patient according to an embodiment. A computer processor receives 1702 vision loss data from a head mounted display (HMD) device worn by a patient, wherein the vision loss data is associated with a vision loss region of an affected eye of the patient. The computer processor then generates 1704 a parameterized perceptual loss model using the vision loss data, and generates 1706 inverse data using the parameterized perceptual loss model. In some implementations, the inverse data is utilized to correct for visual rotational and spatial distortion of the affected eye of the patient. Next, in some implementations the computer processor transmits 1708 the inverse data to the HMD device worn by the patient for use in correcting the visual rotational and spatial distortion loss suffered by the patient, and the process ends. In some implementations, the computer processor also receives additional vision loss data from the head mounted display (HMD) device associated with loss of contrast and loss of color of the affected eye of the patient, generates additional inverse data in the manner described above, and transmits the additional inverse data to the HMD device for use in correcting the loss of contrast and loss of color in the affected eye of the patient.

Figure 18:
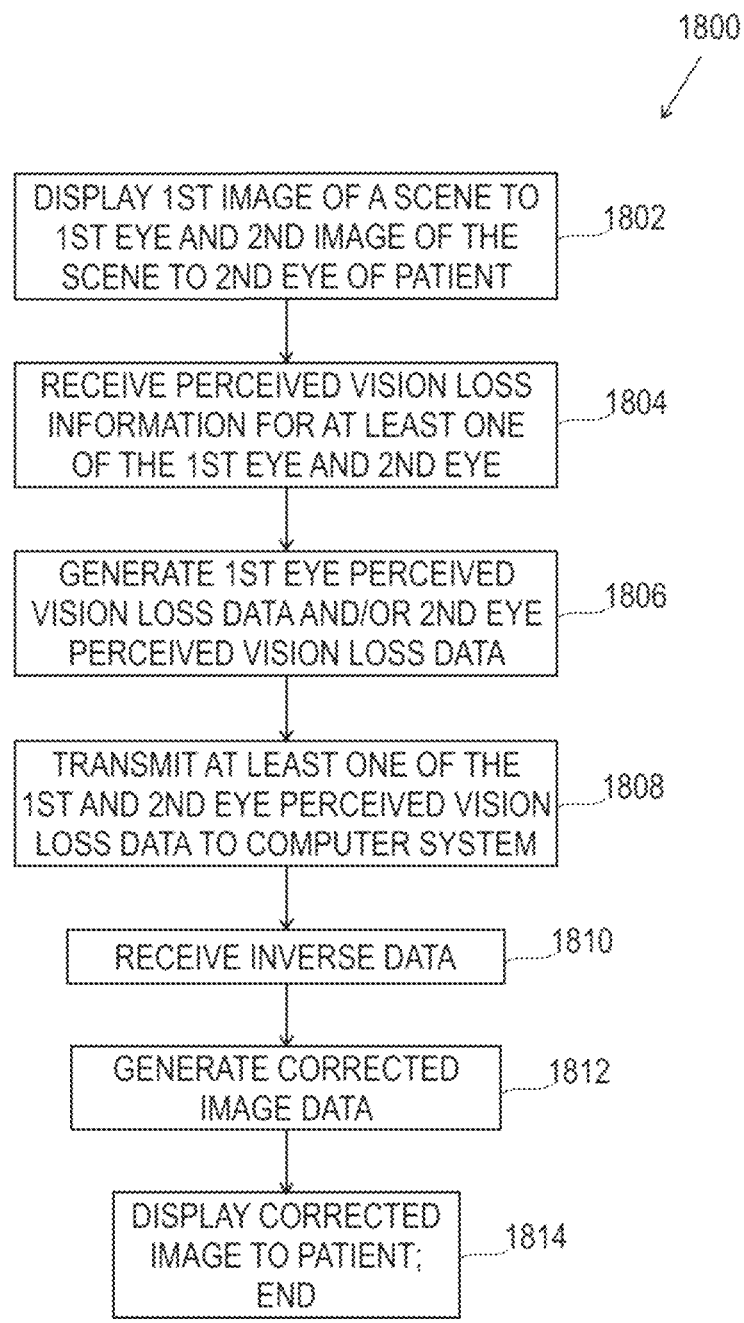
FIG. 18 is a flowchart of a process for simulating and correcting vision loss of a patient according to some embodiments.

FIG. 18 is a flowchart of a process 1800 for simulating and correcting vision loss of a patient according to some embodiments. A head mounted display (HMD) device having first and second display components and worn by a patient displays 1802 a first image of a scene on the first display to a first eye of the patient and a second image of the scene on the second display to a second eye of the patient. The HMD device receives 1804 first perceived vision loss information associated with the first eye and second perceived vision loss information associated with the second eye from the patient and then generates 1806 first perceived vision loss data for the first eye and second perceived vision loss data for the second eye. Next, the HMD device transmits 1808 the first perceived vision loss data and the second perceived vision loss data to a computer system, and then receives 1810 inverse data from the computer system. The inverse data includes at least one of inverse color and luminance desaturation data and inverse rotational and spatial distortion data. The HMD device then generates 1812 at least one of corrected first image data and corrected second image data of the scene and displays 1814 in real time, on at least one of the first display device and the second display device, a corrected image of the scene to the patient based on at least one of the corrected first image data and corrected second image data, and the process ends.

The systems and methods disclosed herein advantageously provide significant tools in a physician's clinical arsenal for diagnosing and monitoring eye conditions causing neural errors at earlier stages of development when potential physiological markers may not be present. In addition, the framework disclosed herein beneficially allows the delivery of robust interventions to compensate for neural errors, in ways not possible using conventional methods. In some embodiments, advances in the fields of Virtual Reality (VR) and Computer Vision (CV) are used in conjunction with the knowledge from current practices in the fields of Ophthalmology and vision science to deliver transformative technologies and methods to address the gaps in diagnosing, monitoring and delivering a robust intervention to compensate for neural errors to a patient. Specifically, as disclosed above a series of visual tests are administered to a patient via Head-Mounted Displays (HMDs) to assess visual function, a parametric model of the functional loss is utilized, and techniques utilized to automatically map the complex relationship between the visual function and the ocular structure. Compensation for the neural errors via a patient-centered and effective intervention is provided by advantageously utilizing virtual and augmented reality (VAMR) headsets or goggles to compensate for neural errors.

As used herein, the term "computer" should be understood to encompass a single computer or two or more computers in communication with each other.

As used herein, the term "processor" should be understood to encompass a single processor or two or more processors in communication with each other.

As used herein, the term "memory" should be understood to encompass a single memory or storage device or two or more memories or storage devices.

As used herein, a "server" includes a computer device or system that responds to numerous requests for service from other devices.

The above descriptions and illustrations of processes herein should not be considered to imply a fixed order for performing the process steps. Rather, the process steps may be performed in any order that is practicable, including simultaneous performance of at least some steps and/or omission of steps.

Although the present disclosure has been described in connection with specific example embodiments, it should be understood that various changes, substitutions, and alterations apparent to those skilled in the art can be made to the disclosed embodiments without departing from the spirit and scope of the disclosure.

What is claimed is:

1. A method for compensating vision loss for a patient comprising:
  receiving, by a computer processor from a head mounted display (HMD) device worn by a patient, vision loss data associated with a vision loss region of an eye of a patient;
  generating, by the computer processor using the vision loss data, a parameterized perceptual loss model;
  generating, by the computer processor using the parameterized perceptual loss model, inverse data to correct for visual rotational and spatial distortion suffered by the eye of the patient;
  generating, by the computer processor, additional inverse data using the parameterized perceptual loss model to correct for color and luminance desaturation; and
  transmitting, by the computer processor, the inverse data and the additional inverse data to the HMD device worn by the patient for use in correcting the visual rotational and spatial distortion and the color and luminance desaturation of the eye of the patient.

2. The method of claim 1, wherein generating the parametrized perceptual loss model comprises:
  determining, by the computer processor utilizing a functional vision loss model, functional vision loss data of the patient; and
  determining, by the computer processor utilizing a physiological vision loss model, physiological vision loss data of the patient.

3. The method of claim 2, wherein the functional vision loss model comprises a parametrization of the vision loss region, a model of contrast sensitivity within the vision loss region, a color sensitivity model, a distortion matrix, and a mapping function representing the spatial distortion within the vision loss region.

4. The method of claim 2, wherein the physiological vision loss model comprises a parametrization of the vision loss region and physiological test parameters obtained from the patient.

5. A system for compensating vision loss of a patient comprising:
  a head mounted display (HMD) device; and
  a computer system comprising a processor operably connected to a storage device, wherein the computer system is operably connected to the HMD device and wherein the storage device includes processor-executable instructions which when executed cause the processor to:
    receive vision loss data associated with a vision loss region of an eye of a patient from the HMD device;
    generate a parameterized perceptual loss model using the vision loss data;
    generate inverse data using the parameterized perceptual loss model, the inverse data for correcting for visual rotational and spatial distortion suffered by the patient; and generate additional inverse data using the parameterized perceptual loss model to correct for color and luminance desaturation; and transmit the inverse data and the additional inverse data to the HMD device worn by the patient for use in correcting the visual rotational and spatial distortion and the color and luminance desaturation of the eye of the patient.

6. The system of claim 5, wherein the instructions for generating the parametrized perceptual loss model comprises further instructions, which when executed cause the processor to:

determine, by utilizing a functional vision loss model, functional vision loss data of the patient; and determine, by utilizing a physiological vision loss model, physiological vision loss data of the patient.

7. The system of claim 6, wherein the functional vision loss model comprises a parametrization of the vision loss region, a model of contrast sensitivity within the vision loss region, a color sensitivity model, a distortion matrix, and a mapping function representing the spatial distortion within the vision loss region.

8. The system of claim 6, wherein the physiological vision loss model comprises a parametrization of the vision loss region and physiological test parameters obtained from the patient.

9. A method for simulating and correcting vision loss of a patient comprising:

displaying, by a head mounted display (HMD) device worn by a patient, an image of a scene on a first display of the HMD device to a first eye of the patient;

receiving, by the HMD device, perceived vision loss information associated with the first eye;

generating, by the HMD device, perceived vision loss data for the first eye;

transmitting, by the HMD device, the perceived vision loss data to a computer system;

receiving, by the HMD device from the computer system, inverse data comprising inverse color and luminance desaturation data and additional inverse data comprising inverse rotational and spatial distortion data;

generating, by the HMD device, corrected image data based on the inverse data and the additional inverse data; and displaying, by the first display of the HMD device in real time, a corrected image of the scene to the patient based on the corrected image data.

10. The method of claim 9, further comprising, prior to generating the perceived vision loss data, performing, by the HMD device, an Inter-Pupillary Distance (IPD) correction.

11. The method of claim 9, wherein displaying a corrected image of the scene comprises utilizing dichoptic masking by using images from a first stereoscopic camera and an associated mask to form a constructed scene for the patient.

12. The method of claim 9, further comprising:

displaying, by the HMD device, a second image of the scene on a second display of the HMD device to a second eye of the patient;

receiving, by the HMD device, second perceived vision loss information associated with the second eye from the patient;

generating, by the HMD device, second perceived vision loss data for the second eye;

transmitting, by the HMD device, the second perceived vision loss data to the computer system;

receiving, by the HMD device from the computer system, second inverse data comprising inverse color and luminance desaturation data and additional second inverse data comprising inverse rotational and spatial distortion data;

generating, by the HMD device, corrected second image data based on the second inverse data and the additional second inverse data; and displaying, by the second display of the HMD device in real time, a corrected image of the scene to the patient based on the corrected second image data.

13. A system for simulating and correcting vision loss of a patient comprising:

a computer system; and a head mounted display (HMD) device operably connected to the computer system, wherein the HMD device comprises a first display for a first eye of the patient and a second display for a second eye of the patient, an HMD processor and a storage device;

wherein the storage device of the HMD device includes processor-executable instructions which when executed cause the HMD processor to:

display an image of a scene on the first display of the HMD device to a first eye of a patient;

receive perceived vision loss information associated with the first eye;

generate perceived vision loss data for the first eye;

transmit the perceived vision loss data to the computer system;

receive inverse data from the computer system, the inverse data comprising inverse color and luminance desaturation data and additional inverse data comprising inverse rotational and spatial distortion data;

generate corrected image data based on the inverse data and the additional inverse data; and display, by the first display in real time, a corrected image of the scene to the patient based on the corrected image data.

14. The system of claim 13, wherein the storage device of the HMD device includes further processor-executable instructions, prior to the instructions for generating the perceived vision loss data, which when executed cause the HMD processor to perform an Inter-Pupillary Distance (IPD) correction.

15. The system of claim 13, wherein the storage device of the HMD device includes further processor-executable instructions which when executed cause the HMD processor to:

display a second image of the scene on the second display of the HMD device to a second eye of the patient;

receive second perceived vision loss information associated with the second eye from the patient;

generate second perceived vision loss data for the second eye;

transmit the second perceived vision loss data to the computer system;

receive second inverse data from the computer system, the second inverse data comprising inverse color and luminance desaturation data and additional second inverse data comprising inverse rotational and spatial distortion data;

generate corrected second image data based on the second inverse data and the additional second inverse data; and display, by the second display in real time, a corrected image of the scene to the patient based on the corrected second image data.

16. The system of claim 15, wherein the HMD device further comprises a first stereoscopic camera and a second stereoscopic camera, and wherein the instructions for displaying a corrected image of the scene comprises processor-executable instructions which when executed cause the HMD processor to utilize dichoptic masking by using images from each of the first stereoscopic camera and the second stereoscopic camera and their associated masks to form a constructed scene for the patient.

17. A head mounted display (HMD) device comprising:
an HMD processor;
a first optical display screen and a second optical display screen operably connected to the HMD processor;
a first camera associated with the first optical display screen and a second camera associated with the second optical display screen, the first and second cameras operably connected to the HMD processor;
a communications device operably connected to the HMD processor; and
a storage device operably connected to the HMD processor, wherein the storage device stores processor-executable instructions which when executed cause the HMD processor to:
 display an image of a scene obtained from one of the first camera on the first display of the HMD device to a first eye of a patient;
 receive perceived vision loss information associated with the first eye from the patient;
 generate perceived vision loss data for the first eye;
 generate inverse data based on the perceived vision loss data, the inverse data comprising inverse color and luminance desaturation data;
 generate additional inverse data based on the perceived vision loss data, wherein the additional inverse data comprises inverse rotational and spatial distortion data;
 generate corrected image data by utilizing the inverse data and the additional inverse data; and
 display, by the first display in real time, a corrected image of the scene to the first eye of the patient based on the corrected image data.

18. The apparatus of claim 17, further comprising an input device operably connected to the HMD processor for use by the patient to provide perceived vision loss information.

* * * * *